United States Patent [19]
Bell et al.

[11] Patent Number: 4,738,845
[45] Date of Patent: Apr. 19, 1988

[54] MODIFIED (115-145) BETA INTERFERONS

[75] Inventors: Leslie D. Bell, Thame; John C. Smith; Paul G. Boseley, both of High Wycombe, all of Great Britain; Michael Houghton, Danville, Calif.

[73] Assignee: G. D. Searle & Co., Chicago, Ill.

[21] Appl. No.: 623,894

[22] Filed: Jun. 25, 1984

[30] Foreign Application Priority Data

Jul. 1, 1983 [GB] United Kingdom ............... 8317880

[51] Int. Cl.$^4$ .................. A61K 45/02; C07K 13/00; C07K 15/26; C12P 21/00
[52] U.S. Cl. .................................. 424/85; 530/351; 435/68; 435/172.3; 435/811
[58] Field of Search ............... 424/85; 435/172.3, 68; 530/351

[56] References Cited

U.S. PATENT DOCUMENTS

| | | | |
|---|---|---|---|
| 4,414,150 | 8/1983 | Goeddel | 435/70 |
| 4,569,908 | 2/1986 | Mark et al. | 435/71 |
| 4,588,585 | 5/1986 | Mark et al. | 435/172.3 |

OTHER PUBLICATIONS

Shepard et al., Nature, vol. 294, pp. 563-565, 1981.

*Primary Examiner*—Blondel Hazel
*Attorney, Agent, or Firm*—Mary Jo Kanady; Paul D. Matukaitis

[57] ABSTRACT

Modified beta interferons containing amino acid substitutions in the beta interferon amino acids 115 to 145 are described. These modified beta interferons exhibit changes in the antiviral, cell growth regulatory or immunomodulatory activities when compared with unmodified be

MODIFIED (115-145) BETA INTERFERONS

BACKGROUND OF THE INVENTION

1. Field of the Invention

This invention describes the use of recombinant DNA technology for the design and synthesis of novel, modified interferons. More specifically the invention relates to interferons not known in nature, which are intended for use in viral and neoplastic diseases, and immunosuppressed and immunodeficient conditions.

2. Description of the Prior Art

The interferons are a class of proteins that occur in vertegrates and act as biological regulators of cell function which include increasing resistance to pathogens, limiting cell growth and modulating the immune system. The most studied property of the interferons is their ability to convert cells into an "antiviral state" during which they are more resistant to virus replication (Lengyel, Annual Review of Biochemistry, 51, 251, 1982). In addition to conferring antiviral resistance to target cells, interferon (IFNs) have antiproliferative (antigrowth) properties (Stewart, 1979, The Interferon System, Springer, Berlin). It has clearly been shown that interferons produced naturally act as antiviral and antiproliferative agents (Gresser et al, Biochim. Biophys. Acta, 516, 231, 1978; J. Exp. Med., 144, 1316, 1976).

The IFNs, by virtue of their antigenic, biological and physico-chemical properties, may be divided into three classes: type I, IFN-α ("leucocyte") and IFN-β ("fibroblast"); and type II, IFN-γ ("immune") (Stewart et al, Nature, 286, 110, 1980). Both genomic DNA and cDNA clones of type I and type II IFNs have been isolated and sequenced, and the potential protein sequences deduced (e.g. Pestka, Arch. Biochem. Biophys, 221, 1, 1983). Whilst in man only one IFN-β and IFN-γ gene are known, human IFN-α is specified by a multigene family comprising at least 20 genes. The classification of IFN-β and IFN-α as type I interferons is in part determined by their significant degree of homology, >23% at the protein level (Taniguchi et al, Nature, 285, 547, 1980).

Whilst the mechanism of action of interferons is not completely understood, certain physiological or enzymatic activities respond to the presence of the interferons. These activities include RNA and protein synthesis. Among the enzymes induced by interferons is (2'-5') (A)n synthetase which generates 2'-5' linked oligonucleotides, and these in turn activate a latent endoribonuclease, RNAse L, which cleaves single-stranded RNA, such as messenger RNA (mRNA) and ribosomal RNA (rRNA). Also induced by IFNs is a protein kinase that phosphorylates at least one peptide chain initiation factor and this inhibits protein synthesis (Lengyel, ibid, p. 253). IFNs have been shown to be negative growth regulators for cells by regulation of the (2'-5') An synthetase activity (Creasey et al, Mol. and Cell Biol., 3, 780, 1983). IFN-β was indirectly shown to be involved in the normal regulation of the cell cycle in the absence of inducers through the use of anti-IFN-β antibodies. Similarly, IFNs have been shown to have a role in differentiation (Dolei et al, J. Gen. Virol., 46, 227, 1980) and in immunomodulation (Gresser, Cell. Immunol., 34, 406, 1977). Finally, IFNs may alter the methylation pattern of mRNAs and alter the proportion of fatty acids in membrane phospholipids, thereby changing the rigidity of cell membranes.

These and other mechanisms may respond to interferon-like molecules in varying degrees depending on the structure of the interferon-like polypeptide. Preliminary evidence (UK Patent No. GB 2 090 258A) suggests that members of the multigene IFN-α family vary in the extent and specificity of their antiviral activity (Pestka, ibid.). For example, combination of IFN-αA with IFN-αD resulted in "hybrid" genes which show antiviral properties that are distinct from either parent molecule (Weck et al, Nucl. Acids Res., 9, 6153, 1981; De La Maza et al, J. IFN Res., 3, 359, 1983; Fish et al, Biochem. Biophys. Res. Commun., 112, 537, 1983; Weck et al, Infect. Immuno., 35, 660, 1982). However, hybrid human IFNs with significantly increased human cell activity/specificty have not yet been developed. One Patent has been published describing IFN-β/α hybrids (PCT/US83/00077). This patent describes three examples, none of which have significantly improved activity. The three examples were constructed using two naturally occurring restriction sites. The resulting hybrid interferons were (1) alpha 1 (1–73)-beta (74–166); (2) beta (1–73)-alpha 1 (74–166); and (3) alpha 61A (1–41)-beta (41–166). These three examples differ structurally from the examples of the present invention. These three examples were based upon the accidental location of two restriction sites and not upon the intentionally designed DNA and amino acid sequences of the present invention.

It is envisaged that a modified interferon will display a new advantageous phenotype. The design and synthesis of new interferon-like polypeptides composed of portions of IFN-β and other amino acid sequences is advantageous for the following reasons:

1. New IFNs can be created which show a greater antiproliferative to antiviral activity (and vice versa) resulting from the selective activation of only some of the normal interferon-induced biochemical pathways.

2. The affinity of hybrid or modified IFNs for cell surface receptors will differ from that of naturally occurring interferons. This should allow selective or differential targeting of interferons to a particular cell type, or increased affinity for the receptor—leading to increased potency against a particular virus disease or malignancy.

3. It will be possible to design novel IFNs which have an increased therapeutic index, thus excluding some of the undesirable side effects of natural IFNs which limit their use (Powledge, T. M., Biotechnology, 2, 214, March 1984).

4. Novel IFNs include in the design structures which allow increased stability to proteolytic breakdown during microbial synthesis.

5. Novel IFNs can be designed to increase their solubility or stability in vivo, and prevent non-specific hydrophobic interactions with cells and tissues.

6. Novel IFNs can be designed which are more readily recovered from the microbial supernatant or extract, and more easily purified.

Additional Relevant Patent Applications

UK No. GB 116 556A—Animal interferons and processes for their production.

U.S. Pat. No. 4 414 150—Hybrid human leukocyte interferons.

SUMMARY OF THE INVENTION

Recombinant DNA technologies were successfully applied to produce modified beta interferon-like polypeptides, nucleic acids (either DNA or RNA) which code for these modified beta interferons, plasmids containing the DNA coding for the modified beta interferons and procedures for the synthesis of these modified beta interferons. Each of the amino acids 115–145 of human beta interferon may individually be replaced by any other amino acid. This replacement may be accomplished in groups of three to twenty-eight amino acids. One preferred embodiment is the replacement of amino acids 115 to 130 of human beta interferon by four to sixteen other amino acids. Another preferred embodiment is the replacement of beta interferon amino acids 121 to 145 by four to twenty-five other amino acids. The beta interferon amino acids 115 to 130 and 121 to 145 may be replaced by corresponding human alpha interferon amino acids. Among the alpha interferons are alpha 1, alpha 2 and alpha H. The alpha and beta interferons from any mammal may be used, including but not limited to humans or other primates, horses, cattle, sheep, rabbits, rats, and mice. Yet another embodiment of the invention discloses the use of the modified beta interferons where in one or more of the antiviral, cell growth regulatory, or immunomodulatory activities is substantially changed from that of the unmodified beta interferon. Particularly preferred embodiments are the amino acid sequence of IFNX411 and 424. Yet another preferred embodiment of the invention is DNA or RNA sequences which code for the synthesis of IFNX411 or 424. Still another embodiment is a plasmid or a cell containing a DNA sequence capable of coding for the synthesis of IFNX411 or 424. Yet another embodiment of the invention is a pharmaceutical composition containing an effective amount of IFNX411 or 424. A final embodiment of the invention is the use of pharmaceutical compositions containing the modified beta interferons in a method of treating viral infections, regulating cell growth or regulating the immune system.

Novel, modified IFNs with increased or decreased biological activity or increased target cell specificity can result in an improved therapeutic index. This should exclude some of the side effects cause by the use in humans of naturally occurring IFNs.

This invention relates to the production in sufficient amounts of novel highly active, and/or highly specific interferon-like molecules suitable for the prophylactic or therapeutic treatment of humans—notably for viral infections, malignancies, and immunosuppressed or immunodeficient conditions.

BRIEF DESCRIPTION OF THE CHARTS AND TABLES

FIG. 1 shows the Sternberg-Cohen 3D model of $\alpha_1$ and $\beta$ interferons (Int. J. Biol. Macromol, 4, 137, 1982).

Chart 2 (a and b) shows the ligated oligonucleotides used in the construction of the novel, modified IFN genes.

Chart 3 (a and b) shows the complete nucleotide sequences of the novel, modified IFN genes and the encoded amino acid sequences.

Chart 4 shows the nucleotide sequence of the trp promoter used to initiate transcription of the novel, modified IFN genes.

Table 1 compares expression, antiviral and antiproliferative activities in bacterial extracts for the novel, modified IFNs.

Tables 2–4 compare the antiviral, antiproliferative and immunostimulting activities of purified IFN-$\beta$ and IFNX411.

DESCRIPTION OF THE PREFERRED EMBODIMENTS

Introduction

Figure 1:
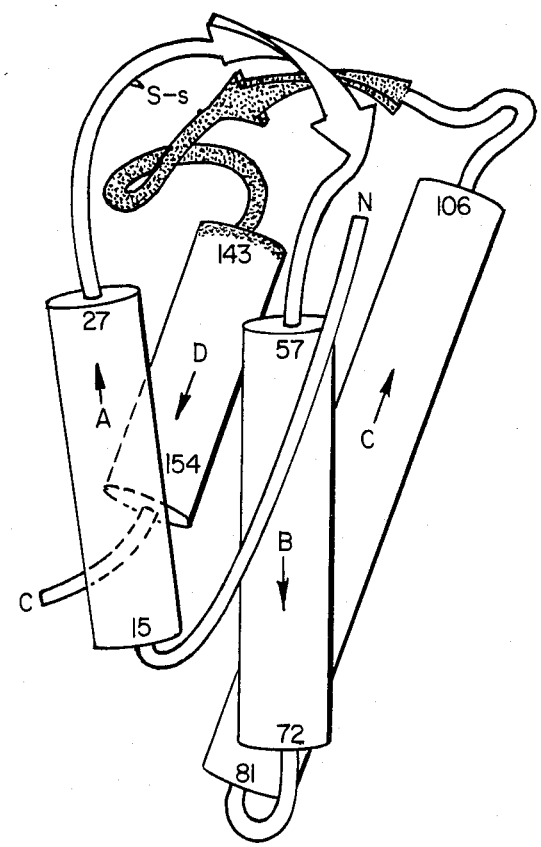
Figure 1:
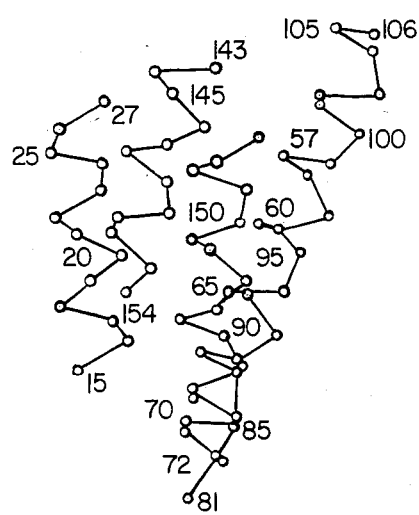
Figure 1:
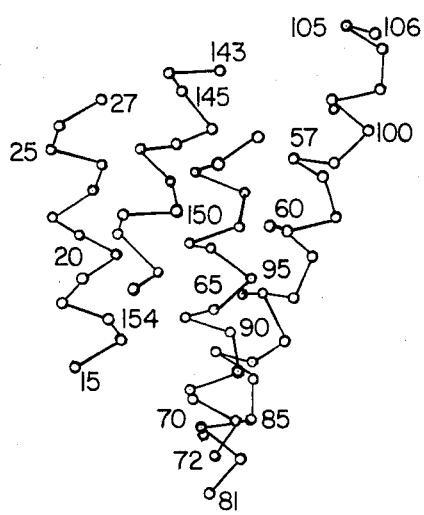

The IFN-$\beta$ gene is a unique gene but shows some significant homologies to the multigenic IFN-$\alpha$ family (Rubinstein, Biochim. Biophys. Acta, 695, 5, 1982). Sternberg and Cohen (Int. J. Biol. Macromol., 4, 137, 1982) have proposed a similar secondary structure for IFN-$\beta$ and IFN-$\alpha_1$. Structure prediction studies suggest four $\alpha$-helices which can be "packed" into a right-handed bundle (FIG. 1) similar to that observed in several unrelated protein structures as determined by X-ray crystallography. The design of some of the modified interferons described herein is derived from our interpretation of the Sternberg/Cohen model. Since IFNs are believed to bind to the same receptor at the cell surface it is possible to introduce variability into IFN-$\beta$ by replacing specific areas with IFN-$\alpha$ segments.

Each amino acid in the 115 to 145 region can be replaced by any other naturally occurring amino acids. The naturally occurring amino acid and their nomenclature are: alanine (Ala or A); valine (Val or V); leucine (Leu or L); isoleucine (Ile or I); proline (pro or P); phenylalanine (Phe or F); tryptophan (Trp or W); methionine (Met or M); glycine (Gly or G); serine (Ser or S); threonine (Thr or T); cysteine (Cys or C); tyrosine (Tyr or Y); asparagine (Asn or N); glutamic acid (Glu or E); lysine (Lys or K) arginine (Arg or R); and histidine (His or H).

The field of the present invention in the design, synthesis and characterization of interferon-like molecules related to IFN-$\beta$ which may have amino acid sequences between IFN-$\beta$ residues 115 and 145 replaced with any other amino acid sequence, unrelated protein sequence, or sequences similar to those of IFN-$\alpha$'s, IFN-$\beta$ or IFN-$\gamma$ found in mammals and other vertebrates.

Though binding of hybrid IFN-$\alpha$'s ($\alpha_1$ and $\alpha_2$ in Streuli et al, Proc. Natl. Acad. Sci. USA, 78, 2848, 1981), an attempt was made to analyse the number and nature of idiotypes involved in the receptor binding site of IFN-$\alpha$'s. Two sites were proposed as constituting the binding site, one in the amino-terminal half and the other in the carboxy-terminal half of IFN-$\alpha$. The two major regions of partial homology between IFN-$\alpha$'s and IFN-$\beta$ occur between amino acid residues 28–80 and 115–151 which may well correspond to the above mentioned idiotypes. Evidence that the 28–80 region may be important in receptor binding come from the finding that polyclonal antibodies raised against a synthetic peptide composed of IFN-$\alpha_2$ amino acids 24–81, bind to IFN-$\alpha_2$ and prevent it interacting with its cell receptor (Dreiding, TNO Interferon Meeting, Rotterdam, 1983). Little is known about the function of the 115–151 region of IFN-$\beta$, which includes the most highly conserved amino acid residues between $\beta$ and $\alpha$ IFNs.

Below are examples of novel, modified IFNs (hereafter called group IV IFNs) wherein amino acid residues between IFN-$\beta$ amino acids 115 and 145 are replaced by other amino acids, e.g. the equivalent amino acid residues from IFN-$\alpha_1$. The examples are to illustrate the invention, and are not intended to limit the scope of the invention in any way. Altered antiproliferative activities are among the novel properties displayed by the group IV IFNs. The following techniques used in the design, chemical synthesis and insertion of DNA fragments in the 115-145 region of the human IFN-$\beta$ gene will be familiar to anyone skilled in the art [see also Molecular Cloning, A Laboratory Manual, eds. Maniatis et al, Cold spring Harbor Laboratories].

Design of the synthetic gene fragments

The nucleotide sequences of each synthetic DNA fragment (Charts 2a and b) were designed utilizing the following criteria:

1. Codon utilization (where it deviates from *natural* IFN-$\beta$ gene sequence) was optimized for expression in *E. coli*. Natural IFN-$\beta$ gene sequences were used as far as possible in order to obtain levels of expression of novel IFNs as high as that of IFN-$\beta$ from plasmid pGC10 ($\sim$4,440 bp) expresses the natural IFN-$\beta$ gene at a high level and is identical to pl/24 (UK Patent Application No. GB 2 068 970A, hereby incorporated by reference) except for the ribosome binding site sequence shown in Chart 4 and the deletion of the $\sim$546 bp BglII-BamHI fragment.

2. Sequences which might anneal to each other in the assembly of the chemically synthesized fragment (Chart 2) were not included in the design (within the limits allowed by the redundancy in the genetic code).

Chemical Synthesis of Gene Fragments

Oligodeoxyribonucleotides were synthesized by the phosphoramidite method (M. H. Caruthers in "Chemical and Enzymatic Synthesis of Gene Fragments", ed. H. G. Basen and A. Lang, Verlag Chemie, 1982, p. 71) on controlled pore glass (H>Koster et al, Tetrahedron, 40, 103, 1984). Fully protected 2'-deoxyribonucleotide 3'-phosphoramidites were synthesized from the protected deoxyribonucleotide and chloro-N,N-(diisopropylamino)methoxyphosphine (L. J. McBride and M. H. Caruthers, Tetrahedron Lett., 24, 245, 1983 and S. A. Adams et al, J. Amer. Chem. Soc., 105, 661, 1983). Controlled pore glass supports were synthesized as described (F. Chow et al, Nucl. Acids Res., 9, 2807, 1981) giving 30-50 $\mu$mol deoxynucleoside per gram.

The functionalised controlled pore glass (50 mg) was treated in a sintered glass funnel at ambient temperature sequentially with:

1. dichloromethane (3 ml, 10 s)
2. 3% (v/v) dichloroacetic acid in dichloromethane (2 ml, 120 s)
3. dichloromethane (3 ml, 10 s)
4. anhydrous acetonitrile (3 ml, 10 s)
5. phosphoramidite monomer (0.06M)/tetrazole (0.23M) in anhydrous acetonitrile (1 ml, 120 s)
6. acetonitrile (3 ml, 10 s)
7. dimethylaminopyridine (0.07M) in acetic anhydride/2,6-lutidine/acetonitrile (1/2/6/ v/v) (1 ml, 60 s)
8. acetonitrile (3 ml, 10 s)
9. iodine (0.2M) in 2,6-lutidine/tetrahydrofuran/water (1/2/2 v/v) (1 ml, 30 s)
10. acetonitrile (3 ml, 10 s)

The cycle was repeated with the appropriate phosphoramidite monomer until the immunogenetic chain was complete. The coupling efficiency of each cycle was monitored by spectrophotometric assay of the liberated dimethoxytrityl alcohol in 10% (w/v) trichloroacetic acid/dichloromethane at 504 nm. After completion of the synthesis, the protecting groups were removed and the oligomer cleaved from the support by sequential treatment with 3% (v/v) dichloroacetic acid/dichloromethane (12 s), thiophenol/triethylamine/dioxan (1/1/2 v/v) (1 h) and concentrated ammonia at 70° C. (4 h). The deprotected oligonucleotides were purified either by HPLC on a Partisil 10 SAX column using a gradient from 1M to 4M triethylammonium acetate pH 4.9 at 50 intracellular or by electrophoresis on a denaturing 15% polyacrylamide gel (pH 8.3).

Ligation of Oligonucleotide Blocks 500 pmole aliquots of the oligonucleotides were phosphorylated with 1 unit of T4 induced polynucleotide kinase in 20 $\mu$l of a solution containing 1000 Ci/pmole [$^{32}$p]$\gamma$-ATP (2.5 Ci/mMole), 100 $\mu$M spermidine, 20 mM DTT, 10 mM MgCl$_2$, 50 mM Tris-HCl (pH 9.0) and 0.1 mM EDTA for 60 minutes at 37° C. The mixtures were then lyophilized and each oligonucleotide purified in a denaturing 15% polyacrylamide gel (pH 8.3). After elution from the gel, the recovery was determined by counting the radioactivity.

Blocks (length 30-50 bases) were assembled by combining 25 pmole of each phosphorylated component with equimplar amounts of the unphosphorylated oligomers from the complementary strand. The mixtures were lyophilized and then taken up in 15 $\mu$l water and 2 $\mu$l 10$\times$ligase buffer (500 mM Tris-HCl pH 7.6, 100 mM MgCl$_2$). The blocks were annealed at 100° C. for 2 minutes, then slowly cooled to room temperature (20° C.). 2 $\mu$l 200 mM DTT and 0.5 $\mu$l 10 mM ATP were added to give final concentrations of 20 mM DTT and 250 $\mu$M ATP in 20 $\mu$l. 1.25 untis of T4 DNA ligase were also added. After 18 hours at 20° C., the products were purified in a 15% polyacrylamide gel under denaturing conditions.

Two duplex blocks were then constructed from the single-stranded pieces. (These were 150 base pairs and 75 base pairs). 1.5 pmole of each block were taken and the mixtures lyophilized. Annealing was carried out in 15 $\mu$l water and 2 $\mu$l 10$\times$ligase buffer at 100° C. for 2 minutes, then slowly cooled to 10° C. 2 $\mu$l 200 mM DTT, 0.5 $\mu$l 10 mM ATP and 1.25 units T4 DNA ligase were added. The reaction was left at 10° C. for 18 hours. The products were then purified in a 10% native polyacrylamide gel.

The final product was assembled by combining 0.4 pmole of the two duplexes. The mixture was lyophilized and then taken up in 15 $\mu$l water and 2 $\mu$l 10$\times$ligase buffer. It was annealed at 50° C. for 2 minutes and then slowly cooled to 10° C. 2 $\mu$l 20 mM DTT, 0.5 $\mu$l 10 mM ATP and 1.25 units ligase were then added and the reaction left at 10° C. for 18 hours. The final product was purified in a 5% native polyacrylamide gel. After elution and ethanol precipitation, the product was taken up in 10 $\mu$l water. 0.5 $\mu$l were removed for counting to calculate the recovery. 2 $\mu$l 10$\times$ligase buffer, 2 $\mu$l 200 mM DTT, 2 $\mu$l 1 mM spermidine, 1 $\mu$l 10 mM ATP, 3 $\mu$l water and 0.5 units kinase were added to the rest (total volume 20 $\mu$l). The reaction was left at 37° C. for 1 hour and stopped by heating at 90° C. for 2 minutes. The final product was ethanol precipitated.

Construction of plasmids expressing novel, modified interferons

This section lists and identifies the vectors employed in the cloning of the synthetic DNA fragments (Chart 2) into the IFN-β coding region, the restriction enzyme sites* used for the insertion, and the rationale for the construction. the positions of these sites* are shown relative to the complete coding nucleotide sequences of the group IV novel IFN genes (Chart 3). The IFN-β (or novel IFN) coding region is shown as a heavy line and would be translated from left to right. The vector sequences between the BamHI site and the EcoRI site are the same as those in pAT153 (equivalent to pBR322 with a 705 bp HaeII fragment deleted—nucleotides 1,646–2,351 on the map). The E. coli trp promoter (Chart 4) lies between the EcoRI site and ClaI site.

1. IFNX411 IFN-β[$\beta^{121-145} \rightarrow \alpha_1^{119-143}$]

This novel, modified IFN was designed to investigate the function of the 115–145 region of IFN-β by substituting an equivalent region from IFN-$\alpha_1$.

Starting vector: pGC206 This vector expresses IFN-β from a part natural (amino acids 1–46) and part synthetic IFN-β gene (amino acids 47–166). It was constructed by replacing the 257 bp EcoRI-PvuII fragment of pMN47 with the equivalent fragment from pI/24C. pMN47 contains an entirely synthetic IFN-β gene (Chart 3c) inserted between the ClaI and BamHI sites of pI/24C, the plasmid containing the entirely natural IFN-β gene. [pI/24C is identical to pI/24 (UK Patent Application No. GB 068 970A) except for the underlined sequences in Chart 4.].

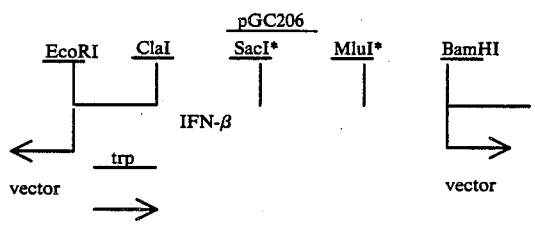

A synthetic oligonucleotide (Chart 2a) was inserted between the SacI* and MluI* sites of pGC206 to give the nucleotide sequence shown in Chart 3a. The resultant IFNX411 gene is expressed on plasmid pGC218.

2. IFNX424 IFN-β[$\beta^{115-130} \rightarrow \alpha_1^{113-128}$]

The rationale and starting vector was the same as for IFNX411 above.

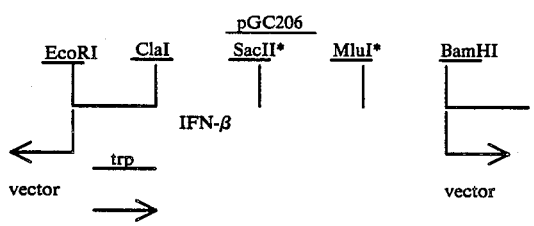

A synthetic oligonucleotide (Chart 2b) was inserted between the SacII* and MluI* sites of pGC206 to give the nucleotide sequence shown in Chart 3b.

The resultant IFNX424 gene is expressed on plasmid pGC217.

Expression of Novel, Modified IFNs in Escherichia coli

All the above mentioned plasmids were grown in E. coli HB101 in the presence of a low level of tryptophan to an $OD_{600}$ of 0.5, then induced for IFN synthesis. The medium (200 ml) contained: M9 salts, 0.5% glucose, 0.1 mM $CaCl_2$, 0.5% Casamino acids, 1 mM $MgSO_4$, 0.1 mg/ml vitamin $B_1$, 2.5 μg/ml tryptophan and 100 μg/ml carbenecillin.

200 ml of medium was inoculated with 2–4 ml of an overnight culture of each clone (in the host E. coli HB101) grown in the above medium except for the presence of 42.5 μg/ml tryptophan, and grown at 37° C. with vigorous aeration. At $OD_{600}$ of 0.5, indole acrylic acid, the inducer of the E. coli trp promoter and therefore also of IFN synthesis, was added to 20 μg/ml. At 4–5 hours after induction 3 ml of culture was withdrawn ($OD_{600}$=0.75–1.2 range) and split as follows: 1 ml was for estimation of total ¢solubilized" IFN antiviral or antiproliferative activity (the activity regained after a denaturation/renaturation cycle); and 1 ml was for display of the total accumulated E. coli proteins plus IFN in a polyacrylamide gel.

(a) Estimation of TOTAL "solubilized" IFN antiviral activity

For recovery of TOTAL "solubilized" IFN antiviral activity, the pellets wre vortexed in 20 μl "lysis buffer" per 0.1 $OD_{600}$ per ml of culture. ("Lysis buffer" is 5M urea, 30 mM NaCl, 50 mM Tris-HCl pH 7.5, 1% SDS, 1% 2-mercaptoethanol, 1% HSA). The mixture was heated for 2–3 minutes at 90° C., frozen at −70° C. for 15 minutes, thawed and centrifuged at 17 K rpm for 20 minutes. The supernatant was diluted in 1 log steps to 1:$10^5$, and appropriate dilutions immediately assayed for IFN antiviral activity by monitoring the protection conferred on Vero cells against the cytopathic effect (cpe) of EMC virus in an in vitro micro-plate assay system (e.g. see Dahl and Degre, Acta. Path. Microbiol. Scan., 1380, 863; 1972). The diluent was 50 mM Tris-Hcl pH 7.5, 30 mM NaCl, 1% human serum albumin (HSA).

(b) Polyacrylamide gel electrophoresis of total polypeptides

Cells from 1 ml of culture were mixed with 10 μl per 0.1 $OD_{600}$ per ml of final sample buffer: 5M urea, 1% SDS, 1% 2-mercaptoethanol, 50 mM Tris-HCl pH 7.5, 30 mM NaCl and 0.05% bromophenol blue. The mixture was heated at 90° C. for 5 minutes, centrifuged for 10 minutes and 5–7 μl loaded on a 15% acrylamide/0.4% bisacrylamide "Laemmli" gel. Electrophoresis was at 70 V for 18 hours. The gel was fixed and stained with Coomassie brilliant blue, then dried and photographed.

(c) Antiproliferative assays of novel, modified interferons

Antiproliferative activity was assessed by the ability of the IFN to inhibit the replication of Daudi lymphoblastoid (Horoszewics et al, Science, 206, 1091, 1979). Daudi cells (in log phase) were cultured for 6 days in 96 well plates in the presence of various dilutions of interferon. The phenol red indicator in the medium changes from red to yellow (more acid) with progressive cell growth. Liquid paraffin was added to prevent pH change on exposure to the atmosphere and the pH change in the medium measured colorimetrically on a Dynatech plate reader. Interferon inhibition of cell growth is reflected by a corresponding reduction in the colour change.

Comparison of IFN protein expression, antiviral activity and antiproliferative activity in bacterial extracts Table 1 sets out the expression levels and antiproliferative and antiviral activities of the group IV novel, modified IFNs in crude bacterial extracts. A range of activities may be given, reflecting natural variation in a biological system or assay. The activity quoted is that which is regained after SDS/urea/mercaptoethanol treatment, by diluting the extract in 1% human serum albumin, as above.

It may be seen in Table 1 that for the control, IFN-$\beta$, antiviral (AV) and antiproliferative (AP) activity vary over not more than a 4-fold range (>20 experiments).

TABLE 1

| Novel, modified IFN | IFNX No. | Expression (% of total cell protein) | EMC/Vero Antiviral activity IU/L/OD$_{600}$ | Daudi cell Antiproliferative activity U/ml at IC$_{50}$* |
|---|---|---|---|---|
| IFN-$\beta[\beta^{115-130}\to\alpha_1^{113-128}]$ | 424 | 3–5 | $9.6 \times 10^6$ | $<10^3$ |
| IFN-$\beta[\beta^{121-145}\to\alpha_1^{119-143}]$ | 411 | 10 | $0.3$–$1.8 \times 10^8$ | $3.5 \times 10^3$ |
| IFN-$\beta$ control | — | 10 | $0.5$–$2 \times 10^8$ | $3.4 \times 10^3$ |

*U/ml at IC$_{50}$ = dilution of sample assayed for antiviral activity giving 50% inhibition of cell growth.

Purification and biological properties of IFNX411

One liter culture was induced and grown to OD$_{600}$ 1–2 as described above. The cell pellet was resuspended in 30 ml 50 mM Tris-HCl pH 8.0 and sonicated on ice, 4×1 min. at 100 W and then centrifuged for 1 hr at 15 K rpm. 30 ml boiling extraction solution (50 mM Tris-HCl pH 8.0, 50 mM DTT and 1–2% SDS) was added, mixed and the solution was sonicated. The solution was then boiled for 5 min., centrifuged for 1 hr at 15 K rpm, and to the supernatant was added (NH$_4$)$_2$SO$_4$ to 40% saturation. After 15 min. the precipitate was collected by centrifugation at 10 K rpm for 20 min. The pellet was redissolved by adding 5 ml warm 50 mM Tris-HCl pH 8.0. Following a 15 K rpm spin for 1 hr, the solution was re-reduced in 50 mM DTT by boiling for 5 min.

The IFNs were fractionated on a 2.35 cm×70 cm column of LKB AcA44 in 0.1% SDS, 50 mM Tris-HCl pH 8.0, and the peak fractions containing 1–2 mg IFN were pooled.

To remove SDS and deplete pyrogens, either (a) the protein was acetone precipitated and redissolved in 50% formic acid, 10% isopropyl alcohol (solvent A); or (b) 6 parts formic acid and 1 part isopropyl alcohol were premixed and added to 3 parts sample. The mixture was applied to C-18 Sep-Pak (capacity greater than 3 mg) or to a C-18 Bond Elut (Anachem). The columns were first washed with solvent A (2–4 ml) and the IFN eluted with 50% formic acid, 50% isopropyl alcohol.

The eluted IFN was dialysed against water to remove formate and then into GuHCl (6M), 100 mM Tris-HCl pH 8.0. To renature the IFN, the sample was reduced in 10 mM DTT at 100° C., then diluted 100-fold into 100 mM Tris-HCl pH 8.0, 200 mM KCl, 1 mM EDTA and either 0.1% Tween 20 or 1% HSA. Protein was estimated prior to biological assay.

Antiviral assays of purified, modified interferons

A single virus (encephalomyocarditis—EMC) was used to determine antiviral activity in primate cells. Determinations were made with a virus cytopathic effect (cpe) assay following challenge of cells of Monkey (Vero) and human (Chang conjunctiva and Searle 17/1 fibroblast) origin (Dahl and Degre, ibid.) Table 2 shows that IFNX411 has similar activity to IFN-$\beta$.

TABLE 2

| Antiviral Activity of Purified Interferon IFNX411 (U/mg IFN Protein) | | | |
|---|---|---|---|
| | 17/1 | CELL LINE CHANG | VERO |
| IFNX411 | $1.1 \times 10^5$ | $1.6 \times 10^6$ | $1.6 \times 10^6$ |
| BETA | $1.9 \times 10^5$ | $7.2 \times 10^5$ | $9.1 \times 10^5$ |
| | | RATIO | |
| IFNX411/BETA | 0.6 | 2.2 | 1.8 |

Antiproliferative assays of purified, novel interferons

Antiproliferative activity was assessed by the ability of the IFN to inhibit the replication of three human cell lines (Horoszewicz et al, Science, 206, 1091, 1979)—Daudi (lymphoblastoid), HEP-2 (carcinoma) and RD (rhabdomyosarcoma). Daudi cells (in log phase) were cultured for 6 days in 96 well plates in the presence of various dilutions of interferon. The phenol red indicator in the medium changes from red to yellow (more acid) with progressive cell growth. Liquid paraffin was added to prevent pH change on exposure to the atmosphere and the pH change in the medium measured colorimetrically on a Dynatech plate reader. Interferon inhibition of cell growth is reflected by a corresponding reduction in the colour change. HEP-2 and RD in log growth were cultured for 3 days in 96 well plates in the presence of interferon. The cells were then fixed with 0.25% glutaraldehyde and stained with methylene blue. After extraction into ethanol the colour intensity was measured on a Dynatech plate reader. Once again colour intensity can be related proportionally to cell growth. In vitro antiproliferative activity of the novel, modified IFNs in crude bacterial extracts was also measured (Daudi cell line only). Table 3 shows that this Daudi cell line is relatively more sensitive to IFNX411 than to IFN-$\beta$.

TABLE 3

| Antiproliferative Activity of Purified IFNX411 (U/mg IFN Protein) | | | |
|---|---|---|---|
| | HEP-2 | CELL LINE RD | DAUDI |
| IFNX411 | $7.1 \times 10^3$ | $9.1 \times 10^3$ | $1.2 \times 10^6$ |
| BETA | $1.3 \times 10^4$ | $1.9 \times 10^4$ | $2.5 \times 10^5$ |
| | | RATIO | |
| IFNX411/BETA | 0.5 | 0.5 | 4.8 |

Stimulation of Antibody-Dependent Cellular Cytoxicity by novel, modified interferons (ADCC)

ADCC represents a cellular system which is immunologically specific, the effect being mediated by antibody. There are several possible versions of this assay. $^{51}$Cr-labelled human red cells (GpA, Rh+ve) sensitised with anti-A antibody using the serum from a Group O individual were incubated with buffy coat cells from a Group O individual. Interferon was assessed by prior overnight incubation with buffy coat cells and its effects compared with those of parallel untreated controls (McCullagh et al, J. IFN Res., 3, 97, 1983). Table 4 shows IFNX411 to have a similar activity to IFN-β with all six donors of buffy coat cells.

TABLE 4

Immunomodulatory (ADCC) Activity of Purified IFNX411 (U/mg IFN Protein)

| | 1 | 2 | 3 | 4 | 5 | 6 |
|---|---|---|---|---|---|---|
| | | | DONOR | | | |
| IFNX411 | $1.4 \times 10^3$ | $3.4 \times 10^4$ | $1.1 \times 10^3$ | $4.7 \times 10^3$ | $3.2 \times 10^3$ | $2.5 \times 10^3$ |
| BETA | $1.5 \times 10^3$ | $2.4 \times 10^4$ | $9.3 \times 10^2$ | $3.0 \times 10^3$ | $4.0 \times 10^3$ | $2.6 \times 10^3$ |
| | | | RATIO | | | |
| IFNX411/BETA | 0.9 | 1.4 | 1.1 | 1.6 | 0.8 | 1.0 |

Pharmaceutical formulation and administration

The novel, modified interferons of the present invention can be formulated by methods well known for pharmaceutical compositions, wherein the active interferon is combined in admixture with a pharmaceutically acceptable carrier substance, the nature of which depends on the particular mode of administration being used. Remington's Pharmaceutical Sciences by E. W. Martin, hereby incorporated by reference, describes compositions and formulations suitable for delivery of the interferons of the present invention. For instance, parenteral formulations are usually injectable fluids that use physiologically acceptable fluids such as saline, balanced salt solutions, or the like as a vehicle. Oral formulations may be solid, e.g. tablet or capsule, or liquid solutions or suspensions.

The novel, modified interferons of the invention may be administered to humans or other animals on whose cells they are effective in various ways such as orally, intravenously, intramuscularly, intraperitoneally, intranasally, intradermally or subcutaneously. Administration of the interferon composition is indicated for patients with malignancies or neoplasms, whether or not immunosuppressed, or in patients requiring immunomodulation, or antiviral treatment. Dosage and dose rates may parallel those employed in conventional therapy with naturally occurring interferons—approximately $10^5$ to $10^8$ units daily. Dosages significantly above or below these levels may be indicated in long term administration or during acute short term treatment. A novel, modified interferon may be combined with other treatments or used in association with other chemotherapeutic or chemopreventive agents for providing therapy against the above mentioned diseases and conditions, or other conditions against which it is effective.

Modifications of the above described modes for carrying out the invention such as, without limitation, use of alternative vectors, alternative expression control systems, and alternative host micro-organisms and other therapeutic or related uses of the novel interferons, that are obvious to those of ordinary skill in the biotechnology, pharmaceutical, medical and/or related fields are intended to be within the scope of the following claims.

CHART 2a

Chemically synthesized sequence for IFNX411

SacI

CCCTGGCTGTTAAGAAATACTTCCGTCGT
TCGAGGGACCGACAATTCTTTATGAAGGGAGCA

ATCACTCTGTACCTGACTGAAAAGAAATAT
TAGTGAGACATGGACTGACTTTTCTTTATA

CTCCTTGTGCTTGGGAGGTTGTA
GAGGAACACGAACCCTCCAACATGCGC

MluI

CHART 2b

Chemically synthesized sequence for IFNX424

SacII

GGTAATGCAGACTCTATTCTGGCTGTAAAGAAATACTTCCGTCGTATCACCCATTACCT
CGCCATTACGTCTGAGATAAGACCGACATTTCTTTATGAAGGCAGCATAGTGGGTAATGGA
GAAAGCTAAAGAATACTCTCACTGCGCATGGACTATTGTA
CTTTCGATTTCTTATGAGAGTGACGCGTACCTGATAACATGCGC

MluI

CHART 3a

IFNX411

IFN—β[IFN—β$^{121-145}$ ⟶ IFN—α$_1^{[19-143]}$]

```
                 5                    10                   15
        MET SER TYR ASN LEU LEU GLY PHE LEU GLN ARG SER SER ASN PHE
        ATG AGC TAC AAC TTG CTT GGA TTC CTA CAA AGA AGC AGC AAT TTT 20                   25                   30
        GLN CYS GLN LYS LEU LEU TRP GLN LEU ASN GLY ARG LEU GLU TYR
        CAG TGT CAG AAG CTC CTG TGG CAA TTG AAT GGG AGG CTT GAA TAC
```

CHART 3a-continued

IFNX411

$$\text{IFN}-\beta[\text{IFN}-\beta^{121-145} \longrightarrow \text{IFN}-\alpha_1^{119-143}]$$

```
              35                    40                    45
CYS LEU LYS ASP ARG MET ASN PHE ASP ILE PRO GLU GLU ILE LYS
TGC CTC AAG GAC AGG ATG AAC TTT GAC ATC CCT GAG GAG ATT AAG 50                    55                    60
GLN LEU GLN GLN PHE GLN LYS GLU ASP ALA ALA LEU THR ILE TYR
CAG CTG CAA CAG TTC CAA AAA GAA GAT GCA GCG CTG ACT ATC TAC 65                    70                    75
GLU MET LEU GLN ASN ILE PHE ALA ILE PHE ARG GLN ASP SER SER
GAA ATG CTG CAA AAC ATC TTC GCG ATC TTC CGT CAA GAC TCT TCC 80                    85                    90
SER THR GLY TRP ASN GLU THR ILE VAL GLU ASN LEU LEU ALA ASN
TCT ACT GGT TGG AAC GAA ACT ATC GTA GAA AAC CTG CTG GCA AAC 95                    100                   105
VAL TYR HIS GLN ILE ASN HIS LEU LYS THR VAL LEU GLU GLU LYS
GTA TAC CAT CAG ATC AAC CAT CTG AAA ACC GTG CTG GAA GAG AAA

SacI
              110                   115              ↓    120
LEU GLU LYS GLU ASP PHE THR ARG GLY LYS LEU MET SER SER LEU
CTG GAA AAA GAA GAC TTC ACC CGC GGT AAA CTG ATG AGC TCC CTG 125                   130                   135
ALA VAL LYS LYS TYR PHE ARG ARG ILE THR LEU TYR LEU THR GLU
GCT GTT AAG AAA TAC TTC CGT CGT ATC ACT CTG TAC CTG ACT GAA

MluI
              140                   145  ↓              150
LYS LYS TYR SER PRO CYS ALA TRP GLU VAL VAL ARG VAL GLU ILE
AAG AAA TAT TCT CCT TGT GCT TGG GAG GTT GTA CGC GTT GAA ATC 155                   160                   165
LEU ARG ASN PHE TYR PHE ILE ASN ARG LEU THR GLY TYR LEU ARG
CTG CGT AAC TTC TAC TTC ATC AAC CGC CTG ACT GGT TAC CTG CGT

ASN ***
AAC TAA 10          20          30          40          50
MSYNLLGFLQ—RSSNFQCQKL—LWQLNGRLEY—CLKDRMNFDI—PEEIKQLQQF—

60          70          80          90          100
QKEDAALTIY—EMLQNIFAIF—RQDSSSTGWN—ETIVENLLAN—VYHQINHLKT—

110         120         130         140         150
VLEEKLEKED—FTRGKLMSSL—AVKKYFRRIT—LYLTEKKYSP—CAWEVVRVEI—

160
LRNFYFINRL—TGYLRN<
```

Chart 3b

IFNX424

IFN—β[IFN—β$^{115-130}$ ⟶ IFN—α$_1^{113-128}$]

```
              5                    10                      15
MET SER TYR ASN LEU LEU GLY PHE LEU GLN ARG SER SER ASN PHE
ATG AGC TAC AAC TTG CTT GGA TTC CTA CAA AGA AGC AGC AAT TTT 20                   25                      30
GLN CYS GLN LYS LEU LEU TRP GLN LEU ASN GLY ARG LEU GLU TYR
CAG TGT CAG AAG CTC CTG TGG CAA TTG AAT GGG AGG CTT GAA TAC 35                   40                      45
CYS LEU LYS ASP ARG MET ASN PHE ASP ILE PRO GLU GLU ILE LYS
TGC CTC AAG GAC AGG ATG AAC TTT GAC ATC CCT GAG GAG ATT AAG 50                   55                      60
GLN LEU GLN GLN PHE GLN LYS GLU ASP ALA ALA LEU THR ILE TYR
CAG CTG CAA CAG TTC CAA AAA GAA GAT GCA GCG CTG ACT ATC TAC 65                   70                      75
GLU MET LEU GLN ASN ILE PHE ALA ILE PHE ARG GLN ASP SER SER
GAA ATG CTG CAA AAC ATC TTC GCG ATC TTC CGT CAA GAC TCT TCC 80                   85                      90
SER THR GLY TRP ASN GLU THR ILE VAL GLU ASN LEU LEU ALA ASN
TCT ACT GGT TGG AAC GAA ACT ATC GTA GAA AAC CTG CTG GCA AAC 95                   100                     105
VAL TYR HIS GLN ILE ASN HIS LEU LYS THR VAL LEU GLU GLU LYS
GTA TAC CAT CAG ATC AAC CAT CTG AAA ACC GTG CTG GAA GAG AAA

SacII
              110              ↓   115                     120
LEU GLU LYS GLU ASP PHE THR ARG GLY ASN ALA ASP SER ILE LEU
CTG GAA AAA GAA GAC TTC ACC CGC GGT AAT GCA GAC TCT ATT CTG 125                  130                     135
ALA VAL LYS LYS TYR PHE ARG ARG ILE THR HIS TYR LEU LYS ALA
GCT GTT AAG AAA TAC TTC CGT CGT ATC ACC CAT TAC CTG AAA GCT

MluI
              140                  145  ↓                  150
LYS GLU TYR SER HIS CYS ALA TRP THR ILE VAL ARG VAL GLU ILE
AAG GAA TAC TCT CAC TGC GCA TGG ACT ATT GTA CGC GTT GAA ATC 155                  160                     165
LEU ARG ASN PHE TYR PHE ILE ASN ARG LEU THR GLY TYR LEU ARG
CTG CGT AAC TTC TAC TTC ATC AAC CGC CTG ACT GGT TAC CTG CGT

ASN ***
AAC TAA
```

```
       10           20           30           40           50
MSYNLLGFLQ—RSSNFQCQKL—LWQLNGRLEY—CLKDRMNFDI—PEEIKQLQQF—

60           70           80           90           100
QKEDAALTIY—EMLQNIFAIF—RQDSSSTGWN—ETIVENLLAN—VYHQINHLKT—

110          120          130          140          150
VLEEKLEKED—FTRGNADSIL—AVKKYFRRIT—HYLKAKEYSH—CAWTIVRVEI—

160
LRNFYFINRL—TGYLRN<
```

CHART 3c

Synthetic IFN-β gene

ClaI

```
                   5
         MET SER TYR ASN LEU LEU
CGA TAA GCT ATG TCT TAC AAC CTG CTG
```

CHART 3c-continued

Synthetic IFN-β gene

PstI

```
        10                      15
GLY PHE LEU GLN ARG SER SER ASN PHE
GGC TTC CTG CAG CGT TCT TCT AAC TTC

20
GLN CYS GLN LYS LEU LEU TRP GLN LEU
CAA TGC CAG AAA CTG CTG TGG CAA CTG
```

CHART 3c-continued
Synthetic IFN-β gene

XmaIII
25 30
ASN GLY ARG LEU GLU TYR CYS LEU LYS
AAC GGC CGC CTG GAA TAC TGC CTG AAA 35 41
ASP ARG MET ASN PHE ASP ILE PRO GLU
GAC CGC ATG AAC TTT GAT ATC CCA GAA

PvuII
45 50
GLU ILE LYS GLN LEU GLN GLN PHE GLN
GAA ATC AAA CAG CTG CAA CAG TTC CAA 55 60
LYS GLU ASP ALA ALA LEU THR ILE TYR
AAA GAA GAT GCA GCG CTG ACT ATC TAC

NruI
65
GLU MET LEU GLN ASN ILE PHE ALA ILE
GAA ATG CTG CAA AAC ATC TTC GCG ATC

HinfI
71 75
PHE ARG GLN ASP SER SER SER THR GLY
TTC CGT CAA GAC TCT TCC TCT ACT GGT 80 85
TRP ASN GLU THR ILE VAL GLU ASN LEU
TGG AAC GAA ACT ATC GTA GAA AAC CTG AccI
90 95
LEU ALA ASN VAL TYR HIS GLN ILE ASN
CTG GCA AAC GTA TAC CAT CAG ATC AAC 100 105
HIS LEU LYS THR VAL LEU GLU GLU LYS
CAT CTG AAA ACC GTG CTG GAA GAG AAA SacII
110
LEU GLU LYS GLU ASP PHE THR ARG GLY
CTG GAA AAA GAA GAC TTC ACC CGC GGT SacI
115 122
LYS LEU MET SER SER LEU HIS LEU LYS
AAA CTG ATG AGC TCC CTG CAT CTG AAA CHART 3c-continued Synthetic IFN-β gene 125 130
ARG TYR TYR GLY ARG ILE LEU HIS TYR
CGC TAC TAT GGT CGT ATC CTG CAT TAC MstI
135 140
LEU LYS ALA LYS GLU TYR SER HIS CYS
CTG AAA GCT AAA GAA TAC TCT CAC TGC 145 150
ALA TRP THR ILE VAL ARG VAL GLU ILE
GCA TGG ACT ATT GTA CGC GTT GAA ATC

155
LEU ARG ASN PHE TYR PHE ILE ASN ARG
CTG CGT AAC TTC TAC TTC ATC AAC CGC

BstEII BamHI
160 166
LEU THR GLY TYR LEU ARG ASN TER
CTG ACT GGT TAC CTG CGT AAC TAA GGA TCC

R<AMSYNLLGFLQRSSNFQCQKLLWQLNGRLEYCLK
DRMNFDIPEEIKQLQQFQKEDAALTIYEMLQNIFAIFRQDS
SSTGWNETIVENLLANVYHQINHLKTVLEEKLEKEDF
TRGKLMSSLHLKRYYGRILHYLKAKEYSHCAWTIVRVE
ILRNFYFINRLTGYLRN<GS

CHART 4

Nucleotide sequence of trp promoter region of IFN-β
expression plasmid pl-24/C

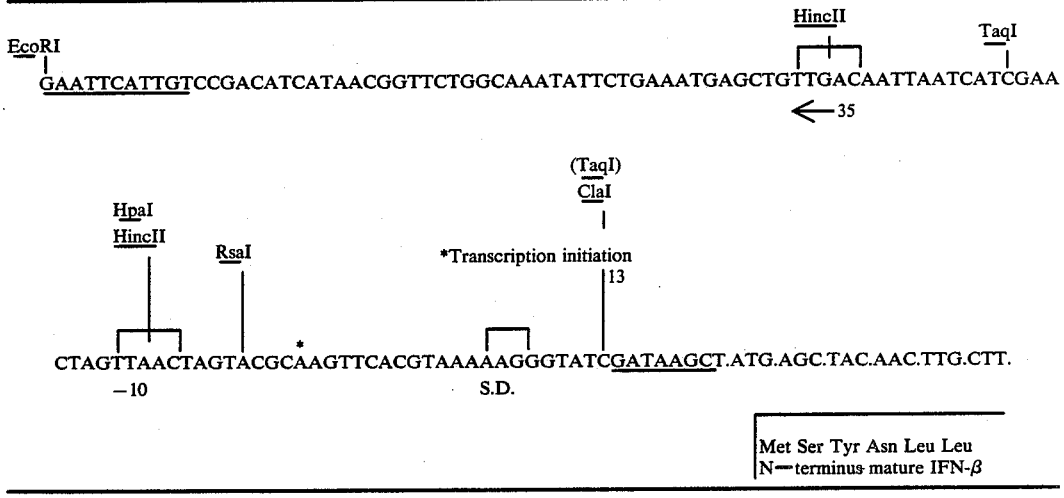

EcoRI HincII TaqI
GAATTCATTGTCCGACATCATAACGGTTCTGGCAAATATTCTGAAATGAGCTGTTGACAATTAATCATCGAA
←35

(TaqI)
ClaI
HpaI
HincII RsaI *Transcription initiation
13
CTAGTTAACTAGTACGCAAGTTCACGTAAAAAGGGTATCGATAAGCT.ATG.AGC.TAC.AAC.TTG.CTT.
−10 S.D.

Met Ser Tyr Asn Leu Leu
N—terminus mature IFN-β

We claim:

1. A modified beta interferon comprising a beta interferon wherein amino acids 121 to 145 of said beta interferon are replaced with amino acids 119 to 143 of alpha 1 interferon.

2. A modified beta interferon comprising a beta interferon wherein amino acids 115 to 130 of said beta interferon are replaced with amino acids 113 to 128 of alpha 1 interferon.

3. A pharmaceutical composition for use in the treatment of viral infections or neoplastic disease or in stimulating the immune system in an animal comprising an effective therapeutic amount of the modified beta interferon of claim 1 admixed with a pharmaceutically acceptable carrier.

4. A pharmaceutical composition for treating viral infections in an animal comprising an effective amount of the modified beta interferon of claim 2 admixed with a pharmaceutically acceptable carrier.

5. A method of treating viral infections in an animal in need of such treatment comprising the administration of an effective amount of a modified beta interferon of claim 1.

6. A method of regulating cell growth in an animal in need of such treatment comprising the administration of an effective amount of a modified beta interferon of claim 1.

7. A method of regulating the immune system in an animal in need of such treatment comprising the administration of an effective amount of a modified beta interferon of claim 1.

* * * * *

UNITED STATES PATENT AND TRADEMARK OFFICE
CERTIFICATE OF CORRECTION

PATENT NO. : 4,738,845

DATED : April 19, 1988

INVENTOR(S) : Bell, et al.

It is certified that error appears in the above-identified patent and that said Letters Patent is hereby corrected as shown below:

Column 2, line 26, reading "-beta (41-166)" should read -- -beta (43-166) --.

Column 2, line 65, reading "UK No. GB 116 556A" should read -- UK No. GB 2 116 556A --.

Column 5, line 21, reading "pGC10" should read -- pGC10 (see Table 1). pGC10 --.

Column 6, line 6, reading "(12 s)," should read -- (120s), --.

UNITED STATES PATENT AND TRADEMARK OFFICE
CERTIFICATE OF CORRECTION

PATENT NO. : 4,738,845
DATED : April 19, 1988
INVENTOR(S) : Bell, et al.

It is certified that error appears in the above-identified patent and that said Letters Patent is hereby corrected as shown below:

Column 7, the first diagram, lines 35-44, reading

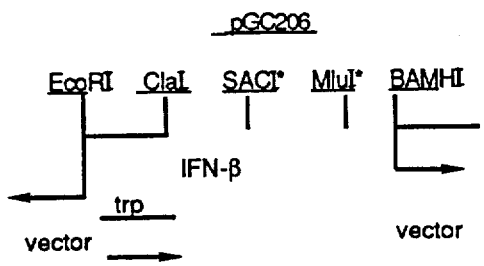

should read

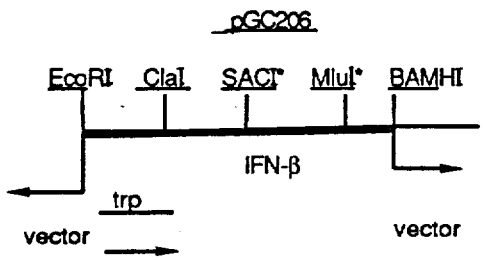

UNITED STATES PATENT AND TRADEMARK OFFICE
CERTIFICATE OF CORRECTION

PATENT NO. : 4,738,845

DATED : April 19, 1988

INVENTOR(S) : Bell, et al.

It is certified that error appears in the above-identified patent and that said Letters Patent is hereby corrected as shown below:

Column 7, the second diagram, lines 54-62, reading

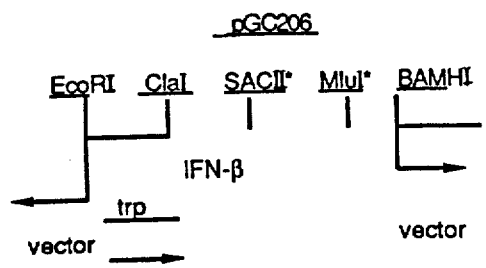

should read

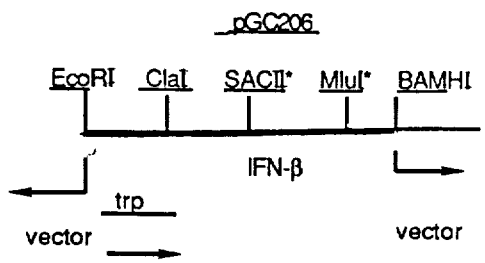

UNITED STATES PATENT AND TRADEMARK OFFICE
CERTIFICATE OF CORRECTION

PATENT NO. : 4,738,845

DATED : April 19, 1988

INVENTOR(S) : Bell, et al.

It is certified that error appears in the above-identified patent and that said Letters Patent is hereby corrected as shown below:

```
Column 12, Chart 2a, lines 40 and 41, reading (both lines together, beginning from the far left), CTC                   TCTC
                GAG    should read   AGAG
```

Signed and Sealed this

Twelfth Day of September, 1989

Attest:

DONALD J. QUIGG

*Attesting Officer*  *Commissioner of Patents and Trademarks*